PDF page image (12) United States Patent
Root et al.

(10) Patent No.: US 10,507,329 B2
(45) Date of Patent: Dec. 17, 2019

(54) IMPLANTABLE MEDICAL DEVICE WITH PROXIMAL CAPTURE FEATURE

(71) Applicant: Cardiac Pacemakers, Inc., St. Paul, MN (US)

(72) Inventors: Michael J. Root, Lino Lakes, MN (US); Nick A. Youker, River Falls, MN (US); Benjamin R. Fruland, Plymouth, MN (US); Keith R. Maile, New Brighton, MN (US); Robert S. Harguth, Ham Lake, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 218 days.

(21) Appl. No.: 14/844,770

(22) Filed: Sep. 3, 2015

(65) Prior Publication Data

US 2015/0375001 A1 Dec. 31, 2015

Related U.S. Application Data

(63) Continuation of application No. 13/029,852, filed on Feb. 17, 2011, now abandoned, which is a continuation of application No. 11/611,658, filed on Dec. 15, 2006, now abandoned.

(60) Provisional application No. 60/750,517, filed on Dec. 15, 2005.

(51) Int. Cl.
*A61N 1/00* (2006.01)
*A61N 1/375* (2006.01)
*A61N 1/372* (2006.01)

(52) U.S. Cl.
CPC .......... *A61N 1/375* (2013.01); *A61N 1/3756* (2013.01); *A61N 1/37211* (2013.01); *Y10T 29/49* (2015.01); *Y10T 29/49002* (2015.01)

(58) Field of Classification Search
CPC ... A61N 1/375; A61N 1/3756; A61N 1/37205
See application file for complete search history.

(56) References Cited

U.S. PATENT DOCUMENTS

| 4,092,464 A | 5/1978 | Dey et al. |
| 4,256,115 A * | 3/1981 | Bilitch ............... A61N 1/0587 607/135 |
| 5,031,618 A | 7/1991 | Mullet |

(Continued)

FOREIGN PATENT DOCUMENTS

| JP | 2291671 A1 | 12/1990 |
| WO | 9415371 A1 | 7/1994 |

(Continued)

OTHER PUBLICATIONS

International Search Report, International Application Serial No. PCT/US2006/048125, 4 pages, dated Aug. 21, 2007.

(Continued)

*Primary Examiner* — Scott M. Getzow
(74) *Attorney, Agent, or Firm* — Seager, Tufte & Wickhem LLP (57) ABSTRACT

The present subject matter includes an implantable medical device with a capture feature at or near the proximal end. In some cases, the capture feature includes a hold that is configured to facilitate a releasable connection with a delivery device that is used to deliver the implantable medical device to a target implant site.

21 Claims, 5 Drawing Sheets

(56) References Cited

U.S. PATENT DOCUMENTS

| | | | |
|---|---|---|---|
| 5,035,965 | A | 7/1991 | Sangyoji et al. |
| 5,511,553 | A | 4/1996 | Segalowitz |
| 5,580,676 | A | 12/1996 | Honda et al. |
| 5,645,586 | A | 7/1997 | Meltzer |
| RE35,746 | E | 3/1998 | Lake et al. |
| 5,776,169 | A | 7/1998 | Schroeppel |
| 5,935,154 | A | 8/1999 | Westlund |
| 6,221,024 | B1 | 4/2001 | Miesel |
| 6,272,379 | B1 | 8/2001 | Fischell et al. |
| 6,273,904 | B1 | 8/2001 | Chen et al. |
| 6,445,948 | B1 | 9/2002 | Somdahl et al. |
| 6,498,951 | B1 | 12/2002 | Larson et al. |
| 6,514,276 | B2 | 2/2003 | Munshi |
| 6,522,525 | B1 | 2/2003 | O'Phelan et al. |
| 6,528,204 | B1 | 3/2003 | Hikmet et al. |
| 6,664,335 | B2 | 12/2003 | Krishnan |
| 6,665,191 | B2 | 12/2003 | Blood et al. |
| 6,676,714 | B2 | 1/2004 | Langan |
| 6,735,474 | B1 * | 5/2004 | Loeb .................. A61N 1/36007 607/41 |
| 6,899,976 | B2 | 5/2005 | Larson et al. |
| 6,961,619 | B2 | 11/2005 | Casey |
| 7,013,739 | B2 | 3/2006 | Schroeder et al. |
| 7,033,322 | B2 | 4/2006 | Silver |
| 7,070,881 | B2 | 7/2006 | Kishiyama et al. |
| 7,120,495 | B2 | 10/2006 | Bardy |
| 7,120,496 | B2 | 10/2006 | Bardy et al. |
| 7,167,751 | B1 * | 1/2007 | Whitehurst .......... A61N 1/3605 607/40 |
| 7,236,829 | B1 * | 6/2007 | Farazi ...................... A61N 1/05 607/2 |
| 7,479,349 | B2 | 1/2009 | O'Phelan et al. |
| 7,509,169 | B2 | 3/2009 | Eigler et al. |
| 7,565,195 | B1 * | 7/2009 | Kroll .................. A61N 1/37288 607/2 |
| 7,860,564 | B2 | 12/2010 | Root et al. |
| 7,985,500 | B2 | 7/2011 | Root et al. |
| 8,301,242 | B2 | 10/2012 | Root et al. |
| 8,311,627 | B2 | 11/2012 | Root et al. |
| 8,532,760 | B2 | 9/2013 | Root et al. |
| 8,644,922 | B2 | 2/2014 | Root et al. |
| 2002/0000034 | A1 | 1/2002 | Jenson |
| 2002/0004167 | A1 | 1/2002 | Jenson et al. |
| 2002/0065373 | A1 | 5/2002 | Krishnan |
| 2002/0090388 | A1 | 7/2002 | Humes et al. |
| 2002/0128546 | A1 | 9/2002 | Silver |
| 2002/0138009 | A1 * | 9/2002 | Brockway ............ A61B 5/0028 600/485 |
| 2002/0193844 | A1 | 12/2002 | Michelson et al. |
| 2003/0149459 | A1 | 8/2003 | Von Arx et al. |
| 2004/0127952 | A1 | 7/2004 | O'Phelan et al. |
| 2005/0189139 | A1 | 9/2005 | Scott |
| 2006/0206162 | A1 * | 9/2006 | Wahlstrand .......... A61N 1/0456 607/46 |
| 2006/0211936 | A1 | 9/2006 | Hu et al. |
| 2007/0099071 | A1 | 3/2007 | Morgan et al. |
| 2007/0092794 | A1 | 4/2007 | Coffey et al. |
| 2007/0099194 | A1 | 5/2007 | Yang et al. |
| 2007/0156184 | A1 | 7/2007 | Root et al. |
| 2007/0156197 | A1 | 7/2007 | Root et al. |
| 2009/0280153 | A1 | 11/2009 | Hunter et al. |
| 2018/0326215 | A1 * | 11/2018 | Ghosh .................. A61N 1/3682 |
| 2019/0083800 | A1 * | 3/2019 | Yang .................. A61N 1/37512 |

FOREIGN PATENT DOCUMENTS

| | | |
|---|---|---|
| WO | 9837926 A1 | 9/1998 |
| WO | 2005047837 A2 | 5/2005 |
| WO | 2007070717 A2 | 6/2007 |

OTHER PUBLICATIONS

Written Opinion, International Application Serial No. PCT/US2006/048125, 6 pages, dated Aug. 21, 2007.

McDonald, Donald A., "The Characteristics of Blood Flow in the Circulation", Chapter 3, Blood Flow in the Arteries, pp. 38-54, (1960).

O'Phelan, "Batteries Including a Flat Plate Design", U.S. Appl. No. 60/437,537, 116 pages, filed Dec. 31, 2002.

Root et al., "Method and Apparatus for Improved Medical Device Profile", U.S. Appl. No. 50/750,517, 30 pages, filed Dec. 15, 2005.

* cited by examiner

IMPLANTABLE MEDICAL DEVICE WITH PROXIMAL CAPTURE FEATURE

CROSS-REFERENCE TO RELATED APPLICATIONS

This application is a continuation of U.S. application Ser. No. 13/029,852, filed on Feb. 17, 2011, which is a continuation of U.S. application Ser. No. 11/611,658, filed on Dec. 15, 2006, which claims the benefit under 35 U.S.C. 119(e) of U.S. Provisional Patent Application Ser. No. 60/750,517, filed Dec. 15, 2005, all of which are hereby incorporated by reference.

The following commonly assigned U.S. patent applications are related and are all incorporated by reference in their entirety: "Batteries Including a Flat Plate Design," U.S. Patent Publication No. 2004/0127952, filed Feb. 7, 2003, "Batteries Including a Flat Plate Design," U.S. Provisional Application Ser. No. 60/437,537 filed Dec. 31, 2002 and "System and Method for Sealing Battery Separator," Ser. No. 11/264,996, filed Nov. 2, 2005.

TECHNICAL FIELD

This disclosure relates generally to implantable medical devices, and more particularly to method and apparatus for improved medical device profiles.

BACKGROUND

Batteries are available to provide energy for self-powered devices. Various chemistries, construction methods, and battery profiles have been developed for use in self-powered devices. But as technology evolves, new applications would benefit from new battery configurations. For example, known applications could benefit from improvements in battery chemistries, constructions methods, and battery profiles. Specifically, improved battery profiles could enable improved device profiles, which could widen the range of possible implantation locations. Such a range would widen, in part, because improved shapes could address existing problems, such as non-preferred levels of hemodynamic drag, turbulence, fluid sheer stress and stagnation.

Improved batteries should provide as much electrical performance as existing battery designs. Additionally, new designs should be compatible with efficient manufacturing methods. Further, new designs should offer a wide range of configurations to make possible various applications.

SUMMARY

The above-mentioned problems and others not expressly discussed herein are addressed by the present subject matter and will be understood by reading and studying this specification.

One embodiment of the present subject matter includes an implantable device which includes an implantable electronics shell and an implantable power source shell wherein an exterior of the implantable device is defined in part by an exterior of the implantable electronics shell and an exterior of the implantable power source shell.

Another embodiment of the present subject matter includes a method for shaping a housing for an implantable device which includes modeling the exterior to provide reduced hydrodynamic drag in conditions measured at the implant site, modeling the exterior to provide reduced turbulence in conditions measured at the implant site, modeling the exterior to provide reduced fluid sheer stress in conditions measured at the implant site and/or modeling the exterior to provide reduced stagnation in conditions measured at the implant site.

Yet another embodiment of the present subject matter includes a system which includes an implantable medical device having a handle and a positioning lead having a clasp adapted to removably couple with the handle.

The present subject matter covers embodiments which include power sources which are batteries. Some embodiments include power sources which are capacitors. Various electronics are contemplated, including cardiac rhythm management electronics, neurostimulation electronics, wireless communications electronics, ultrasonic transducer electronics, and others. The present subject matter extends to embodiments which shape a shell, and dispose a transducer, a wireless transmitter, and a power source in the shell. The present subject matter extends to systems which include implantable devices which are sized for passage through a guide catheter, with sensor positioning leads sized for slidable disposition in the guide catheter. Other features are contemplated as well.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Various embodiments of the present subject matter include implantable medical devices. In various embodiments, implantable sensors are discussed. Implantable sensors, in various embodiments, are self-powered measurement devices. In some embodiments, these devices provide a wireless signal to one or more receivers. Receivers may be located in vivo or ex vivo. A transceiver relationship is additionally possible, in various embodiments, in which bidirectional communications between a sensor and a receiver are conducted.

Implantable sensors should be as compact as possible to provide improved patient comfort and to ease the difficulties facing care providers during the implantation procedure. An implantation which is less invasive than prior designs is preferred. As some embodiments are intended for endovascular use, several design parameters are important. For example, to provide a device which is compatible with some applications, it is important to provide an implantable device which provides a reduced hydrodynamic drag over existing designs. Some applications would benefit from reduced turbulence. Some applications would benefit from reduced fluid sheer stress. Some applications would benefit from reduced stagnation. Applications which are not tuned in light of one or more of these criteria can provide non-preferred performance. Non-performing applications can pair with other risk factors and lead to an embolus or another non-preferred condition.

The present subject matter provides an implantable medical device, in various embodiments, which features an improved profile for implanted use. In some embodiments, the profile provides improved performance for endovascular use.

Figure 1:
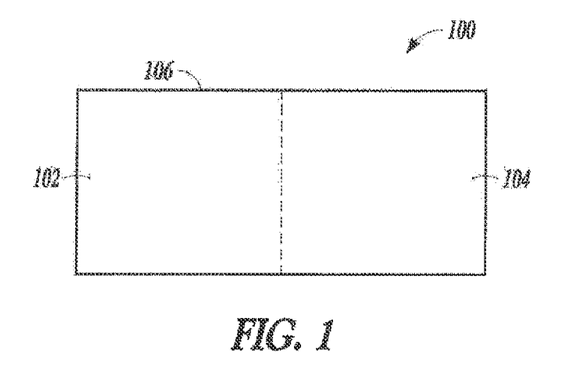
FIG. 1 shows a schematic of an implantable medical device, according to one embodiment of the present subject matter.

FIG. 1 shows a schematic of an implantable medical device 100, according to one embodiment of the present subject matter. Various embodiments of the present subject matter include electronics 104. Additionally, in various embodiments, a power source 102 is included. The implantable device 100 can be symmetrical along three, two, or no axes, in various embodiments. In various embodiments, the device includes a device shell 106. In some of these embodiments, the device shell 106 is hermetically sealed. In some embodiments, the device shell 106 is partially defined by a case which houses electrodes for the power source 102. A power source 102, in various embodiments, includes a battery. In an additional embodiment, the power source 102 includes a capacitor.

Electronics 104, in various embodiments, include various components. Some embodiments include components adapted to communicate energy with devices external to the implantable medical device 100. In some of these embodiments, the energy is communicated wirelessly. Embodiments within the present subject matter include, but are not limited to, ultrasonic transducers, inductive transducers, and other wireless transducers.

Additional components are included as well. Electronics 104 include, in various embodiments, components for wireless communication of information to devices external to the implantable medical device. Additionally, in various embodiments, electronics 104 include sensor electronics which communicate data. Some of these embodiments include a pressure transducer. Also, in some embodiments, electronics 104 include stimulation electronics. Some of these embodiments include neurostimulation electronics. Some embodiments include a processor interconnected to other components to assist other components in communicating with each other. These components are not an exhaustive or exclusive list of components contemplated by the present subject matter, as the present subject matter additionally extends to components not expressly listed herein.

In various embodiments, the device shell includes a profile which improves fluid flow. In some embodiments, the shell profile reduces hydrodynamic drag, turbulence, fluid sheer stress, and/or stagnation. In some embodiments, the shell is elongate. Some of these embodiments include a shell which is elongate, and which includes portions which have a circular cross section. An elongate shell is useful for implantation in a blood vessel in a manner which reduces hydrodynamic drag, turbulence, fluid sheer stress, and/or stagnation. Various embodiments include applications which have a profile adapted for implantation in a vein or in an artery. Various embodiments use an elongate shell in which the power source 102 and electronics 104 are stacked in a column along the interior of the elongate shell. In additional embodiments, the power source 102 and the electronics 104 are disposed side-by-side along the length of the elongate shell.

In various embodiments, hydrodynamic drag, turbulence, fluid sheer stress, and/or stagnation are determined using computational fluid dynamics. In some embodiments, measurements are taken of a target implant site. In some of these embodiments, the measurements are used to determine the shape of an implantable medical device which reduces hydrodynamic drag, turbulence, fluid sheer stress, and/or stagnation.

Some embodiments do not base modeling for reduced hydrodynamic drag, turbulence, fluid sheer stress, and/or stagnation on the measurement of an individual implant site. In some embodiments, the shape of the shell is determined based on reduced hydrodynamic drag, turbulence, fluid sheer stress, and/or stagnation in a statistically significant hypothetical model. For example, in some embodiments, a patient population is measured, and a model having blood-flow characteristics which typify the population is created. This model is used in the creation of a shell which reduces hydrodynamic drag, turbulence, fluid sheer stress, and/or stagnation, in various embodiments.

In some of these embodiments, a power source 102 is created to fill a portion of the interior of the implantable medical device in a manner which limits the amount of unused space. In some of these embodiments, the power source 102 is made from a stack of substantially planar power source 102 electrodes. Some embodiments use a stack of substantially planar power source 102 electrodes having different layers perimeters. Such a stack can have contours which are adapted to efficiently adhere to all or a portion of the interior space of the implantable medical device. Additional embodiments can use wound electrodes.

Battery embodiments having shapes which are determined as a function of improved fluid flow also fall within the scope of the present scope, including, but not limited to, battery embodiments having a prismatic shape, a generally cylindrical shape, and other shapes fall within the present scope.

In various embodiments, the implantable medical device 100 is adapted for reduced invasion during surgery. For example, in some embodiments, a profiles is used which delivers reduced tissue damage. Various embodiments include a profile having reduced tissue damage includes an elongate device having a length of from about 5 millimeters to about 10 millimeters. Devices up to 5 millimeters are possible, in various embodiments. Additional embodiments use devices of over ten millimeters. Additionally, various embodiments includes a profile which an average width of from about 1 millimeter to about 3 millimeters. Some embodiments are sized up to 1 millimeter. Additional embodiments are sized over 3 millimeters. Various embodiments are cylindrical, and are from about 5 to 10 millimeters long, and about 1 to 3 millimeters in diameter. Some embodiments are around 2.5 millimeters in diameter. Some embodiments are greater than 3 millimeters in diameter. Additionally, some embodiments are longer than 10 millimeters.

In some embodiments, the implantable medical device is elongate, with a proximal portion and a distal portion. In various embodiments, during implantation, the device is grasped at the proximal portion, and the distal portion is led through vasculature. In some of these embodiments, the distal portion has one or more edges. Edges, in various embodiments, are rounded to reduce tissue damage during implantation. Profiles which reduce tissue damage may also be included. For example, implantable medical devices having a parabolic distal portion fall within the present scope. Some of these embodiments are bullet shaped. Other profiles not expressly listed herein are additionally encompassed by the present scope.

In one process of the present subject matter, a profile of the implantable medical device 100 is determined as a function of power and size requirements. Power requirements, in various embodiments, are determined by the number of energy use events which occur during implantation. In some embodiments around 33 milliamp-hours are consumed per month, for example. It is understood that other devices using other power and size requirements are contemplated to be within the scope of this invention.

In some of these embodiments, power requirements are further defined by battery efficiency. Battery efficiency, in various embodiments, is a function of self-leakage. Power requirements are further determined by battery type. For example, some embodiments use primary batteries. Some embodiments use secondary batteries. Secondary batteries enable recharging. Recharging, in various embodiments, is depending on patient compliance. Recharging frequency should be reduced to increase patient satisfaction.

In an additional process of the present subject matter, a power requirement is determined and a power source 102 profile is selected to satisfy the power requirement and to satisfy a size requirement which reduces invasiveness. In some of these embodiments, a power management algorithm is developed to comply with these constraints. In some of these embodiments, a secondary power source 102 is used. In some of these embodiments, a power source 102 charging algorithm is used to improve power source 102 profile and the reduce requirements to a patient to visit a clinic to recharge the power source 102. In various embodiments, an iterative process of selecting a profile, and selecting a power management algorithm is used to determine the final profile of power source 102 which meets predetermined therapeutic requirements.

Various embodiments incorporate battery chemistries compatible with the present configurations. Embodiments within the present scope include, but are not limited to, at least one of a metal oxide, a metal sulfide, a metal selenide, a metal halide, a metal oxyhalide compound, and corresponding lithiated forms. Some of these embodiments include at least one of manganese, vanadium, silver, molybdenum, tungsten, cobalt, nickel, chromium, and main group compounds such as carbon monofluoride and iodine. Additionally, some embodiments include at least one of carbon, lithium, sodium, potassium, rubidium, cesium, magnesium, calcium, strontium, barium, tin, zinc or silver.

Primary battery chemistry embodiments fall within the present scope. Additionally, secondary battery chemistry embodiments fall within the present scope. In some embodiments a power source of an implantable medical device includes a plurality of batteries connected in series, parallel or a combination of series and parallel.

Various electrode constructions fall within the present scope. Embodiments compatible with the present subject matter include monolithic electrodes, pelleted electrodes, and other electrodes which have a solid shape. Pelleted electrodes, in various embodiments, include pellets formed from compressed powder, dough or slurry. Some electrode embodiments are formed from a tightly wound ribbon which is wound unto itself without an insulator to separate progressive wraps from one another. Additionally, some embodiment include an electrode onto which is pressed or coated an electronically conductive material. Other electrode configuration embodiments compatible with the present subject matter additionally fall within the present scope.

Additionally, various battery profiles using these electrodes fall within the present scope. Embodiments with the present scope include, but are not limited to, batteries having a cylindrical shape, batteries having a prismatic shape, batteries having a button shape, and batteries having other shapes. In some examples, batteries have shape which is determined as a function of the shape's impact on reducing blood flow. In some examples, batteries have shape which is determined as a function of the shape's impact on reducing tissue damage during implantation.

Figure 2:
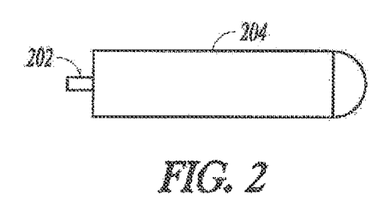
FIG. 2 shows a side view of an implantable medical device having a semi-spherical shaped portion, according to one embodiment of the present subject matter.

FIG. 2 shows a side view of an implantable medical device having a semi-spherical shaped portion, according to one embodiment of the present subject matter. In various embodiments, a protrusion 202 extends from the main portion 204 of the implantable device. The protrusion 202 is useful, in various embodiments, for positioning the device in a target implant site. For example, in some embodiments, a positioning lead grasps the device at protrusion 202. Protrusion 202 includes a texture, in various embodiments. For example, some embodiments of protrusion 202 include knurling. In various embodiments, the positioning lead positions the device while connected to the implantable device at the protrusion 202. In various embodiments, the positioning lead releases the implantable medical device. In various embodiments, the protrusion 202 provides a handle which is compatible with a clasp of a positioning lead, but in some embodiments, a protrusion is not included, and a positioning lead grasps the main body of the implantable medical device.

Figure 3:
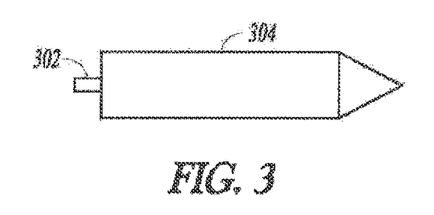
FIG. 3 shows a side view of an implantable medical device having a polyhedral portion, according to one embodiment of the present subject matter.

FIG. 3 shows a side view of an implantable medical device having a polyhedral portion, according to one embodiment of the present subject matter. The implantable medical device pictured includes a protrusion 302, and a main portion 304. The main portion 304 is shaped like a polyhedron, in some embodiments. In additional embodiments, it is cone shaped.

Figure 4:
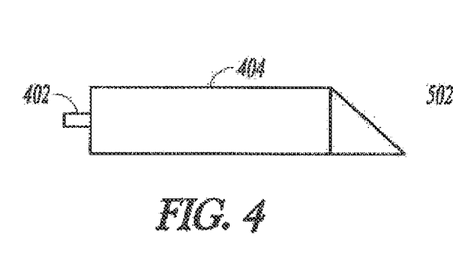
FIG. 4 shows a side view of an implantable medical device having a polyhedral portion, according to one embodiment of the present subject matter.

FIG. 4 shows a side view of an implantable medical device having a polyhedral portion, according to one embodiment of the present subject matter. The implantable medical device pictured includes a protrusion 402, and a main portion 404. The pictured embodiment has a chisel shape.

Figure 5:
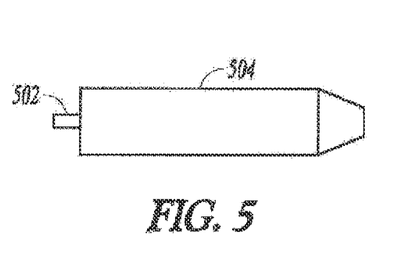
FIG. 5 shows a side view of an implantable medical device, according to one embodiment of the present subject matter.

FIG. 5 shows a side view of an implantable medical device, according to one embodiment of the present subject matter. The implantable medical device pictured includes a protrusion 502, and a main portion 504. In various embodiments, the implantable medical device has a distal portion which is shaped like a cone with the tip missing. In additional embodiments, the main portion 504 is a polyhedron. In some embodiments, the main portion 504 is bullet shaped.

The shapes described and pictured herein do not define an exhaustive or an exclusive list of the possible shapes within the present subject matter. Additional shapes fall within the present scope. For example, additional shapes which reduce hydrodynamic drag, turbulence, fluid sheer stress, and/or stagnation, fall within the present scope.

In various embodiments, an implantable medical device includes an improved shape enabled by the use of a battery which includes stacked electrodes. In some of these embodiments, the contour of the stack is non-linear, enabling the stack to occupy space within an implantable medical device efficiently. Additionally, in some embodiments, the battery is a coil.

Figure 6:
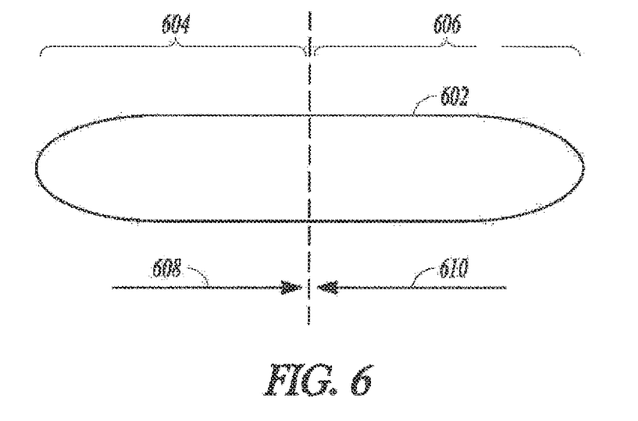
FIG. 6 shows a side view of an implantable medical device, according to one embodiment of the present subject matter.

FIG. 6 shows a side view of an implantable medical device, according to one embodiment of the present subject matter. The device 602 includes a first portion 604 which has a first profile shaped as a function of hydrodynamic drag, turbulence, fluid sheer stress, and/or stagnation. The device additionally includes a second portion 606 which has a second profile shaped as a function of hydrodynamic drag, turbulence, fluid sheer stress, and stagnation.

Blood flow is known to be bidirectional in a blood vessel. Additionally, as the heart pumps blood, the rate of blood flow of blood varies across a cross section of a blood vessel. Therefore, improved medical device embodiments are designed to offer increased performance in reducing hydrodynamic drag, turbulence, fluid sheer stress, and/or stagnation. The present subject matter includes a device having a first portion 604 which is shaped to offer improved compatibility with blood flow direction 608, in various embodiments. In some of these embodiments, the present subject matter includes a second portion 606 which is shaped to offer improved compatibility with blood flow direction 610. Blood flow direction 608 is approximately collinear with blood flow direction 610, in various embodiments.

Figure 7:
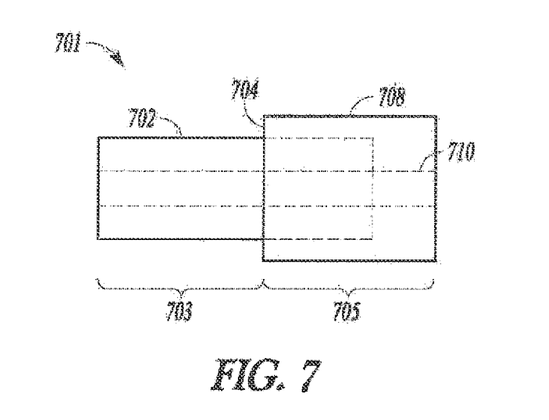
FIG. 7 shows a side view of an implantable medical device, according to one embodiment of the present subject matter.

FIG. 7 shows a side view of an implantable medical device, according to one embodiment of the present subject matter. In various embodiments, the device includes a first shell portion 703. In additional embodiments, a second shell portion 705 is attached to the first shell portion 703. The first shell portion 703 and the second shell portion 705 are hermetically sealed to one another with a hermetic seal 704, in various embodiments. Hermetic seals include welds, resins, and additional types of known hermetic seals.

In various embodiments, the first shell portion 702 doubles as a case for a battery. For example, in some embodiments, a battery anode and cathode are disposed in a case 702. Battery case embodiments include a drawn case portion mated to another case portion, in some examples. In some of these examples, a drawn case portion is sealed to another case portion with a battery case seal. In embodiments where the implantable medical device 701 requires a hermetically sealed exterior, and the battery case seal is exposed to the environment of the implantable medical device, the battery case seal is hermetic. In embodiments where the battery case seal is not exposed to the environment, the battery case seal may not be hermetic. For example, in some non-hermetic embodiments, the battery case seal is adapted to resist the flow of battery electrolyte.

The implantable medical device 701, in various embodiments, includes an optional cavity 710. In various embodiments, the cavity passes through the implantable medical device 701. In additional embodiments, the cavity does not pass through the implantable medical device 701, but instead defines an interior cavity.

An optional cavity 710, in various embodiments, is defined by a cylindrical opening which is concentric to an overall cylindrical shape of the implantable medical device 701, in some embodiments. Some configurations of the present subject matter are toroidally shaped. Some shapes of the present subject matter resemble an extruded toroid. In various embodiments, the cavity is irregular.

Figure 8:
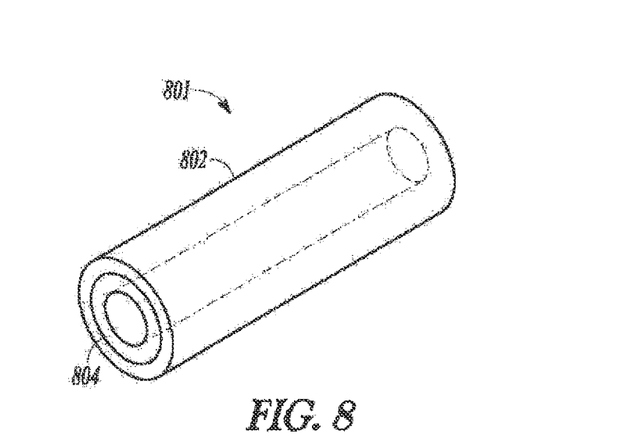
FIG. 8 shows a perspective view of an implantable medical device, according to one embodiment of the present subject matter.

FIG. 8 shows a perspective view of an implantable medical device, according to one embodiment of the present subject matter. In various embodiments, an implantable medical device 801 includes a first portion 804 and a second portion 802. In some embodiments, the second portion 802 includes electronics. Some of these embodiments include pressure transducers. In additional embodiments, the second portion 802 includes a battery. In some of the embodiments, the battery is housed in the case which is the same as the exterior of the second portion 802.

In some embodiments, the first portion 804 includes electronics. Some of these embodiments include pressure transducers. In additional embodiments, the first portion 804 includes a battery. In some of the embodiments, the battery is housed in the case which is the same as the exterior of the first portion 804.

In some embodiments, the first portion 804 extends through the second portion 802. In some of these embodiments, a cavity extends through the first portion 804. A cavity assists in improving performance with respect to hydrodynamic drag at the implant site, turbulence at the implant site, fluid sheer stress at the implant site, and/or stagnation at the implant site. For example, in some embodiments, a cavity discourages emboli formation.

Figure 9:
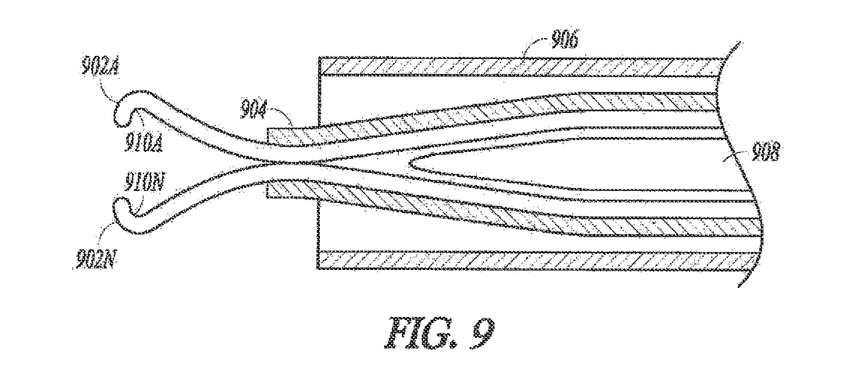
FIG. 9 shows a cross section of an IMD deployment tool, according to one embodiment of the present subject matter.

FIG. 9 shows a cross section of an IMD deployment tool, according to one embodiment of the present subject matter. In various embodiments, the present subject matter includes a positioning lead for physical manipulation of an implantable medical device. Implantable medical devices should be deployed in a manner which reduced invasive damage. To this end, it is beneficial to utilize techniques which employ catheters which can reduce damage to patient tissues.

Catheter techniques are used in present embodiments which enable the catheter to remain in place for a predetermined period of time. For example, in one embodiment, a catheter is left in place for approximately 30 minutes. In various embodiments, during the time a catheter is in place, health care professionals are able to position an implantable medical device. Additionally, an implantable medical device may undergo a validation sequence to ensure proper function, in various embodiments. If the implanted device is improperly positioned, it may be adjusted while the catheter is in place. If the implanted device does not pass required validation criterion, it may be extracted and replaced with a replacement device.

Various embodiments of the present subject matter include a guide catheter 906. In various embodiments, the guide catheter 906 is implanted in the patient, with a proximal portion positioned nearby a health care professional operating the catheter, and with a distal portion positioned near a target implant site. A positioning lead 903 is disposed through the guide catheter 906 in various embodiments. In various embodiments, the positioning lead 903 is slidably disposed in the guide catheter 906.

In various embodiments, the positioning lead 903 includes a clasp at a distal portion. In some of these embodiments, the clasp includes claws 902A-N. In various embodiments, two claws are included. In various embodiments, more than two claws are included. Various embodiments include claws which are adapted to grasp, in pairs, opposite sides of an object. In some embodiments, each claw is equidistant from another. In additional embodiments, claws are irregularly spaced while grasping an object. In one embodiment having two claws, the claws are spaced at 180 degree intervals around an implantable medical device. In an embodiment having four claws, the claws are spaced at 90 degree intervals around an implantable medical device. Claw configurations not expressly listed herein also fall within the present scope. Claw material, in various embodiments, includes nitinol, stainless steel, titanium, and/or other materials. Other materials exist that are not expressly listed herein and fall within the present scope.

The present subject matter includes claws which have features 910A-N sized to receive a mating feature of an implantable medical device. Some embodiments include features having a texture. One texture includes knurling. Additional textures include ribbing. This list is not exhaustive or exclusive, and additional features and textures are possible without departing from the scope of the present subject matter.

In various embodiments, an oversheath 904 is disposed over the claws 902A-N. In various embodiments, the claws are formed having a bias which encourages movement of the claws away from one other but for a constraint nearby the claws. In some embodiments, the oversheath provides such a constraint. In various embodiments, when the oversheath is moved away from the grasping features of the claws, the claws are able to move away from one another. Such behavior, in various embodiments, provides for a mechanism with which a grasped implantable medical device may be released. The oversheath 904, in various embodiments, includes one or more of a polyimide, TEFLON, PEBAX, and/or additional materials not listed herein. TEFLON is a registered trademark of E. I. Du Pont de Nemours and Company, 1007 Market St., Wilmington Del. 19898.

PEBAX is a registered trademark of Arkema Corporation France, 4-8 Cours Michelet 92800, Puteaux France.

Additionally, some embodiments include a pushwire 908 which may be used use push an implantable medical device away from the claws 902A-N. A guidewire is also used, in some embodiments. In various embodiments, the pushwire is biocompatible. In some embodiments, the pushwire is metallic. Various embodiments include MP35N, stainless steel, titanium, and/or additional metals, for example. Some materials used include corrosion resistant alloys. In additional embodiments, the pushwire is a nonmetallic material. One embodiment includes TEFLON. TEFLON is a registered trademark of E. I. Du Pont de Nemours and Company Corporation, 101 West 10$^{th}$ St., Wilmington Del. 19898. Additional materials not expressly listed herein are also within the present scope.

Various pushwire shapes are within the present subject matter. Pushwire 908 functions to push an implantable medical device away form the claws 902A-N, in various embodiments. In additional embodiments, pushwire 908 functions to separate the claws 902A-N such that a grasped implantable medical device is released.

Figure 10:
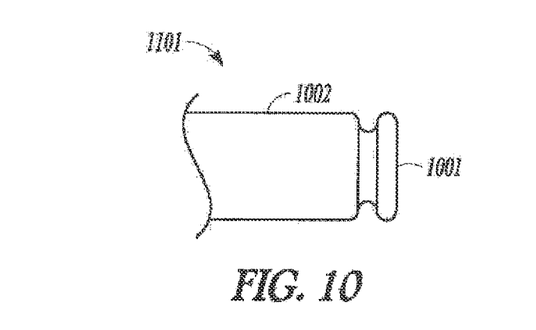
FIG. 10 shows a side view of an IMD, according to one embodiment of the present subject matter.

FIG. 10 shows a side view of an IMD, according to one embodiment of the present subject matter. The implantable medical device 1001, in various embodiments, includes electronics and a power source. In some embodiments, the electronics include a pressure transducer. In various embodiments, the implantable medical device 1001 is hermetically sealed.

In various embodiments, the implantable medical device 1001 includes a ridge 1004. In various embodiments, the ridge is a rim. In additional embodiments, the implantable medical device 1001 includes a protrusion which is shaped otherwise. For example, in some embodiments, the protrusion is a boss. In some embodiments, the protrusion is polyhedral. Additional features are used for mating to grasping features of a positing tool. For example, some embodiments have discrete pockets shaped to match features of a clasp. The ridge, or additional features discussed herein, do not comprise an exhaustive or exclusive list, and additional interface designs are within the present scope.

In some of these embodiments, the ridge has a diameter which is approximately the same as the internal diameter of a guide catheter. For example, in one embodiment, a non-flexed guide catheter has a lumen which is cylinder shaped, and which has a diameter which is sized for passage an implantable medical device.

Figure 11:
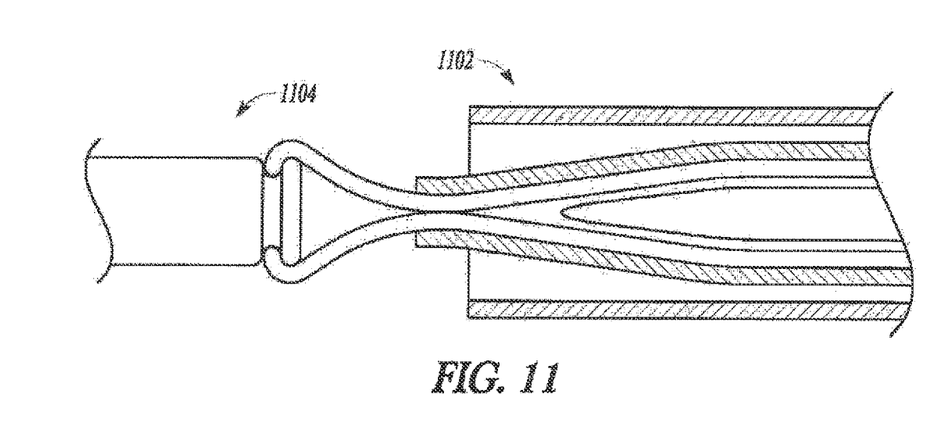
FIG. 11 shows a partial cross section of an IMD deployment system, according to one embodiment of the present subject matter.

FIG. 11 shows a partial cross section of an IMD deployment system, according to one embodiment of the present subject matter. The illustration shows one mode of operation, in which an implantable medical device 1104 is grasped by a positioning lead 1102.

In various embodiments, a cavity is provided on an implantable medical device. In some embodiments, a clasp is collapsed with an oversheath. A collapsed clasp is inserted into a cavity in various embodiments. Various embodiments release the clasp into the cavity in order to secure the implantable medical device to the clasp. In various embodiments, deployment of the implantable medical device includes positioning the oversheath to again collapse the clasp so that the clasp can be removed from the cavity. In some embodiments, the cavity is located in the center of a face of an implantable medical device. The locations set forth herein are demonstrative and are not intended to be exclusive or exhaustive. Additional locations fall within the present scope.

Figure 12:
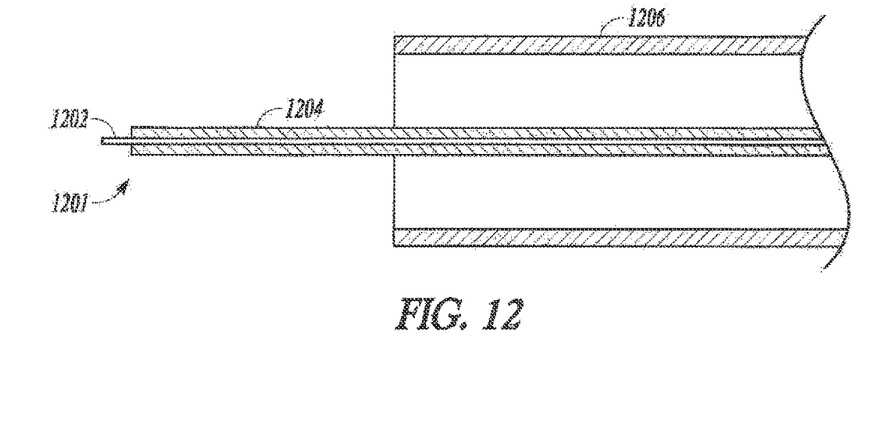
FIG. 12 shows a cross section of an IMD deployment tool, according to one embodiment of the present subject matter.

FIG. 12 shows a cross section of an IMD deployment tool, according to one embodiment of the present subject matter. Various embodiments of the present subject matter include a guide catheter 1206. In various embodiments, a positing tool 1201 is disposed in a lumen of the guide catheter 1206. In various embodiments, the positing tool 1201 includes a flexible sheath 1204. In various embodiments, extending through the flexible sheath is a pushwire 1202. In some embodiments, the pushwire 1202 is slidably interference fitted into the flexible sheath 1204. In various embodiments, the flexible sheath 1204 is not interference fit to the sheath 1204 once the pushwire 1202 is removed from the flexible sheath 1204. Embodiments of the present subject matter include a method of positioning an implantable medical device. Some of these embodiments include removing the pushwire 1202. Embodiments include removing a sheath 1204 in which the pushwire is only partially disposed. Some of these embodiments include removing a sheath 1204 when the pushwire is sufficiently removed from the lumen of the sheath such that the pushwire 1202 is not disposed through an opening of the implantable medical device.

Figure 13A:
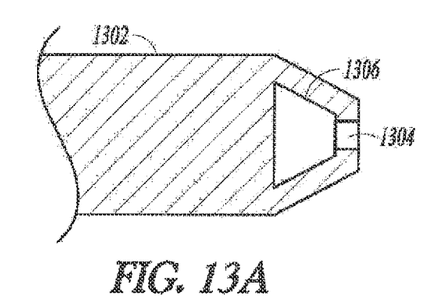
FIG. 13A shows a side view of an IMD, according to one embodiment of the present subject matter.
Figure 13B:
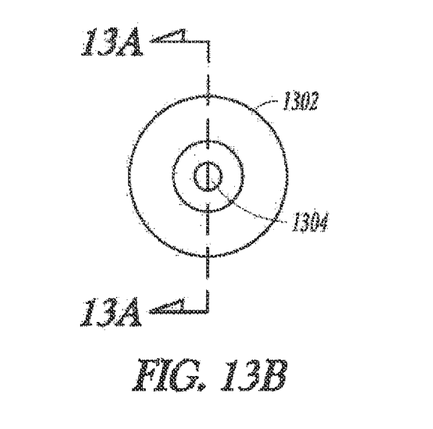
FIG. 13B shows a front view of an IMD, according to one embodiment of the present subject matter.

FIG. 13A shows a side view of an IMD, according to one embodiment of the present subject matter. In various embodiments, the implantable medical device 1302 includes an opening 1304. In some embodiments, the opening is cylinder shaped. The opening 1304, in various embodiments, provides access to opening 1306, in various embodiments. FIG. 13B shows a front view of an IMD, according to one embodiment of the present subject matter.

Figure 14:
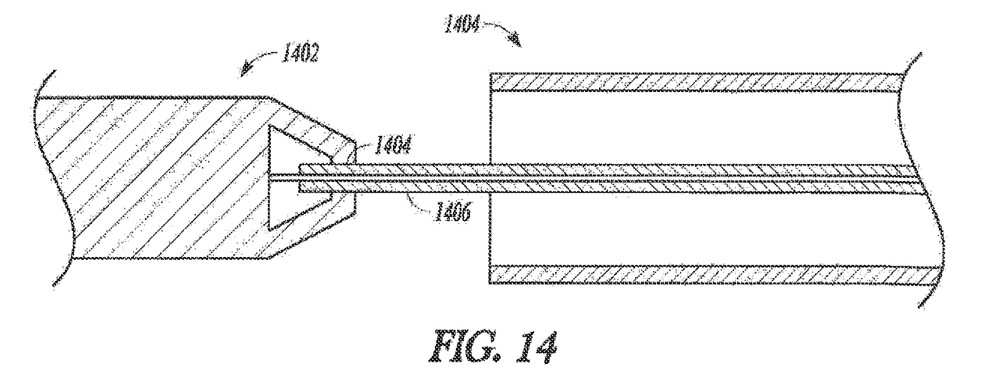
FIG. 14 shows a partial cross section of an IMD deployment system, according to one embodiment of the present subject matter.

FIG. 14 shows a partial cross section of an IMD deployment system, according to one embodiment of the present subject matter. In various embodiments, the present system, in a deployment state, disposes the guidewire through the flexible sheath in an area proximal the opening 1404. The flexible sheath 1406, in various embodiments, is moved from a state which is not interference fitted to opening 1404, to a state which is interference fitted to opening 1404. As such, in the deployment state, the flexible sheath is interference fitted with opening 1404, in various embodiments.

Figure 15:
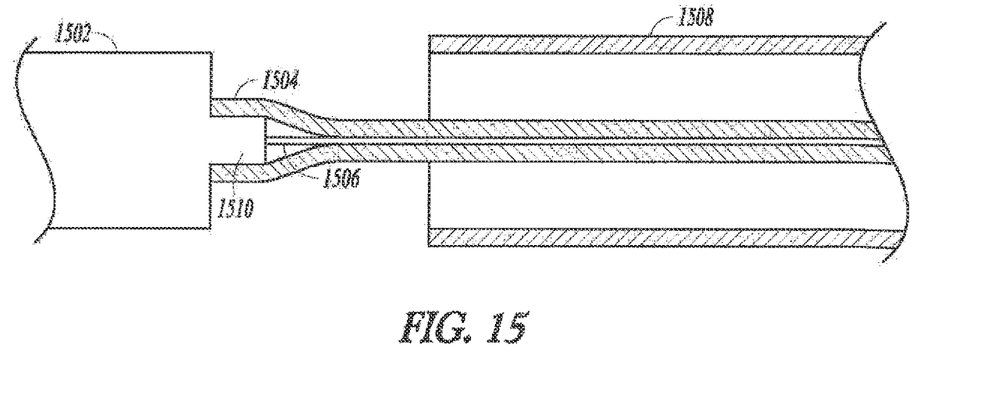
FIG. 15 shows a partial cross section of an implantable medical device, according to one embodiment of the present subject matter.

FIG. 15 shows a partial cross section of an implantable medical device, according to one embodiment of the present subject matter. Various embodiments of the present subject matter include an implantable medical device 1502. Additionally included is a protrusion 1510 of the implantable medical device. Various embodiments additionally include a guide catheter 1508 as well.

The present subject matter, in various embodiments, includes a sleeve 1504. In some embodiments, the sleeve is flexible. In additional embodiments, the sleeve is a membrane. Various sleeve 1504 embodiments include PEBAX, silicone, SANTOPRENE, and/or additional materials. SANTOPRENE is a registered trademark of Advanced Elastomer Systems, L.P. Limited Partnership Assignee of Delaware, 388 S. Main Street, Akron, Ohio 44311-1059. The sleeve 1504, in various embodiments, is interference fit to the protrusion 1510. In various embodiments, a push wire extends through a lumen in sleeve 1504. In various embodiments, a health care professional can pull the sleeve away form the implantable medical device 1502, and out of contact with protrusion 1504, which pushing against protrusion 1502 with the pushwire 1506. As such, a worker is able to deploy the implantable medical device 1502 at an implant site.

Figure 16:
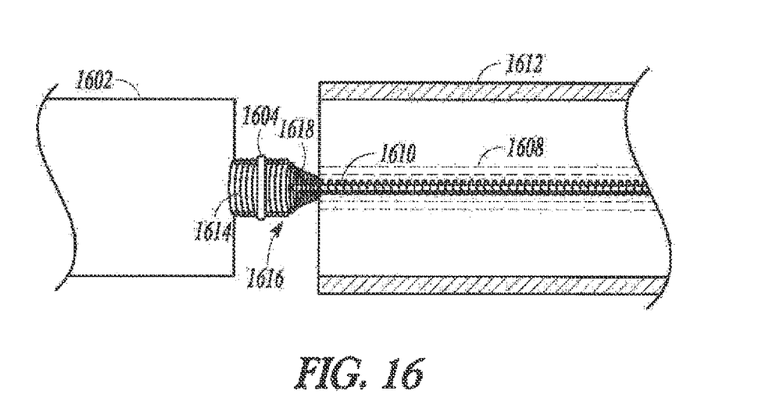
FIG. 16 shows a partial cross section of an implantable medical device, according to one embodiment of the present subject matter.

FIG. 16 shows a partial cross section of an implantable medical device, according to one embodiment of the present subject matter. Various embodiments of the present subject matter include an implantable medical device 1602. Additionally included is a protrusion 1514 of the implantable medical device. In some embodiments, the protrusion 1514 includes a collar 1604. Additional embodiments include features such as textures, depressions, or additional features. For example, in some embodiments, a depression rings the protrusion 1614.

Various embodiments additionally include a guide catheter 1612. Disposed through the guide catheter, in various embodiments, is a positioning lead 1616. Positioning lead, in various embodiments, includes a proximal portion, located external a patient, and a distal portion. The distal portion of the positioning lead 1616 is positioned proximal an implant site in use, in various embodiments. In some embodiments, a substantially coiled filament 1618 is wrapped around the protrusion 1614.

The coiled filament 1618, in some embodiments, extends along the positioning lead 1616. In some embodiments, the coiled filament 1618 defines the exterior of the positing lead 1616. In some embodiments, a positing lead includes a first portion which does not include the coiled filament 1618, and which is connected to the coiled filament 1618 at a distal portion of the positioning lead 1616. In some of these embodiments, the connection between the first portion and the coiled filament 1618 includes a molded fit. In some of these embodiments, the first portion is molded over the coiled filament 1618.

In some embodiments, a coiled portion of the positioning lead 1616, which includes portions adapted for wrapping around a protrusion 1614, is disposed in a sheath 1608. A sheath can benefit a positioning lead by providing a bias, by protecting a coiled filament, and by providing a structure which has a lower instance of axial compression than does a coiled filament.

In various embodiments, a push wire 1610 is disposed through the positioning lead. The push wire 1610, in various embodiments, is adapted for pushing the implantable medical device 1602, away from the positioning lead 1616. In various embodiments, as the implantable medical device 1602 is pushed away from the positioning lead 1616, the coiled portions which are wrapped around a protrusion unwrap. Such embodiments function to both position and deploy the implantable medical device 1602. This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A leadless cardiac pacemaker configured for endovascular use, comprising:
   an elongated housing configured for endovascular use, the elongated housing including an elongated main body portion extending between a proximal end region and a distal end region, the elongated main body portion having a length and a width that is transverse to the length;
   electronics housed by the main body portion of the elongated housing;
   the electronics including stimulation electrodes operatively coupled to the electronics;
   a battery housed by the main body portion of the elongated housing for powering the electronics; and
   a connection feature extending proximally from the main body portion and proximally of the stimulation electrodes, the connection feature configured to facilitate a releasable connection with another device, the connection feature comprising a narrowed neck extending proximally from the proximal end region of the main body portion of the elongated housing to a widened head.

2. The leadless cardiac pacemaker of claim 1, wherein the electronics comprises cardiac rhythm management electronics.

3. The leadless cardiac pacemaker of claim 2, wherein the electronics comprises communication electronics.

4. The leadless cardiac pacemaker of claim 1, wherein the electronics comprises wireless communication electronics.

5. The leadless cardiac pacemaker of claim 1, further comprising one or more sensors operatively coupled to the electronics.

6. The leadless cardiac pacemaker of claim 1, wherein the narrowed neck has a curved concave longitudinal cross-sectional profile.

7. The leadless cardiac pacemaker of claim 6, wherein the widened head has a curved convex longitudinal cross-sectional profile.

8. The leadless cardiac pacemaker of claim 1, wherein the main body portion of the elongated housing is cylindrical shaped and has a first diameter along at least part of its length, and the widened head has an outer extending perimeter that is circular in shape with a second diameter.

9. The leadless cardiac pacemaker of claim 8, wherein the first diameter is the same as the second diameter.

10. A leadless cardiac pacemaker configured for endovascular use, comprising:
- an elongated housing configured for endovascular use, the elongated housing including a cylindrical shaped main body portion extending between a proximal end region and a distal end region, the cylindrical shaped body having a length and a width that is transverse to the length;
- cardiac rhythm management electronics housed by the main body portion of the elongated housing;
- the cardiac rhythm management electronics including stimulation electrodes operatively coupled to the electronics;
- communication electronics housed by the main body portion of the elongated housing;
- a battery housed by the main body portion of the elongated housing for powering the cardiac rhythm management electronics, the stimulation electrodes, and the communication electronics; and
- a connection feature extending proximally from the main body portion and proximally of the stimulation electrodes, the connection feature configured to facilitate a releasable connection with another device, the connection feature comprising a narrowed neck extending from the proximal end region of the elongated housing to a widened head, the narrowed neck having a width that is less than the width of the cylindrical shaped main body portion and the widened head having a width that is wider than the width of the narrowed neck.

11. The leadless cardiac pacemaker of claim 10, wherein the narrowed neck has a curved concave longitudinal cross-sectional profile.

12. The leadless cardiac pacemaker of claim 11, wherein the widened head has a curved convex longitudinal cross-sectional profile.

13. The leadless cardiac pacemaker of claim 10, wherein the cylindrical shaped main body portion has a first diameter, and the widened head has an outer extending perimeter that is circular in shape with a second diameter.

14. The leadless cardiac pacemaker of claim 13, wherein the first diameter is the same as the second diameter.

15. The leadless cardiac pacemaker of claim 10, wherein the battery and the cardiac rhythm management electronics are stacked in a column arrangement along the length of the main body portion of the elongated housing.

16. The leadless cardiac pacemaker of claim 10, wherein the battery and the cardiac rhythm management electronics are disposed in a side-by-side arrangement along the length of the main body portion of the elongated housing.

17. A leadless cardiac pacemaker configured for endovascular use, comprising:
- an elongated housing configured for endovascular use, the elongated housing including a main body portion extending between a proximal end region and a distal end region, the main body portion having a length and a width that is transverse to the length;
- cardiac rhythm management electronics housed by the main body portion of the elongated housing;
- stimulation electrodes housed by the main body portion of the elongated housing, operatively coupled to the electronics;
- communication electronics housed by the main body portion of the elongated housing;
- a battery housed by the main body portion of the elongated housing for powering the cardiac rhythm management electronics, the stimulation electrodes, and the communication electronics; and
- a connection feature extending proximally from the main body portion and proximally of the stimulation electrodes, the connection feature comprising a narrowed neck extending from the proximal end region of the elongated housing to a widened head, the narrowed neck having a width that is less than the width of the main body portion and the widened head having a width that is wider than the width of the narrowed neck.

18. The leadless cardiac pacemaker of claim 17, wherein the narrowed neck has a curved concave longitudinal cross-sectional profile.

19. The leadless cardiac pacemaker of claim 17, wherein the widened head has a curved convex longitudinal cross-sectional profile.

20. The leadless cardiac pacemaker of claim 17, wherein the main body portion has a cylindrical shape and has a first diameter, and the widened head has an outer extending perimeter that is circular in shape with a second diameter.

21. The leadless cardiac pacemaker of claim 20, wherein the first diameter is equal to the second diameter.

* * * * *